United States Patent [19]

Higashide et al.

[11] 4,229,533

[45] Oct. 21, 1980

[54] METHOD FOR PRODUCING ANTIBIOTIC C-15003 P-4

[75] Inventors: Eiji Higashide, Takarazuka; Kazunori Hatano; Mitsuko Asai, both of Takatsuki, all of Japan

[73] Assignee: Takeca Chemical Industries, Ltd., Osaka, Japan

[21] Appl. No.: 959,471

[22] Filed: Nov. 13, 1978

[30] Foreign Application Priority Data

Nov. 18, 1977 [JP] Japan .................................. 52-139384

[51] Int. Cl.³ .............................................. C12P 17/18
[52] U.S. Cl. ...................................... 435/119; 435/872
[58] Field of Search ................ 435/118, 119, 253, 872

[56] References Cited

U.S. PATENT DOCUMENTS

| | | | |
|---|---|---|---|
| 3,902,968 | 9/1975 | Inamine et al. | 435/253 |
| 4,110,166 | 8/1978 | Mori et al. | 435/872 |
| 4,151,042 | 4/1979 | Higashide et al. | 435/119 |
| 4,162,940 | 7/1979 | Higashide et al. | 435/119 |

Primary Examiner—Thomas G. Wiseman
Attorney, Agent, or Firm—Stevens, Davis, Miller & Mosher

[57] ABSTRACT

A novel Antibiotic C-15003 P-4 is specifically produced by cultivating a microorganism of the genus Nocardia in a culture medium containing leucine and/or its derivatives.

The Antibiotic C-15003 P-4 is useful as an antifungal agent, antiprotozoan agent and antitumor agent.

3 Claims, No Drawings

METHOD FOR PRODUCING ANTIBIOTIC C-15003 P-4

This invention relates to a method for producing Antibiotic C-15003 P-4 in an industrially advantageous method.

Antibiotic C-15003 P-4 (hereinafter, abbreviated as "P-4".) is a novel compound obtained by cultivating a microorganism of the genus Nocardia, which is isolated from natural sources.

The microorganisms employable in the present invention, when cultured by the use of conventional culture media, generally produce several components of Antibiotic C-15003 simultaneously. For separating each component from the cultured broth, very complicated processes are required, which inevitably invites a low yield of the component desired.

With the purpose of overcoming this drawback, the present inventors have made extensive study, especially, for recovering P-4 specifically, and found that P-4 can be produced with a remarkably high ratio to the total content of Antibiotic C-15003, when the culture medium of a specific composition is employed.

Thus, the present invention is a method for producing Antibiotic C-15003 P-4 characterized in that said method comprises cultivating a microorganism belonging to the genus Nocardia and capable of producing Antibiotic C-15003 P-4 (hereinafter sometimes called "Antibiotic C-15003 P-4-producing strain".) in a culture medium containing leucine or its derivatives or salts thereof to specifically produce Antibiotic C-15003 P-4 in the cultured broth, and recovering the Antibiotic C-15003 P-4.

In the context of this invention, the term "Antibiotic C-15003" or "C-15003" means, generically, the four compounds having the following general formula (I) as a group, or a mixture of two or three of said compounds or, severally, any one of the same compounds.

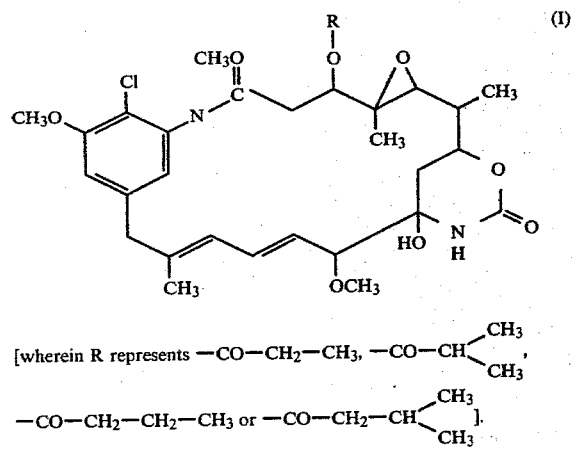

[wherein R represents —CO—CH$_2$—CH$_3$, —CO—CH$\begin{smallmatrix}CH_3\\CH_3\end{smallmatrix}$, —CO—CH$_2$—CH$_2$—CH$_3$ or —CO—CH$_2$—CH$\begin{smallmatrix}CH_3\\CH_3\end{smallmatrix}$ ].

Referring to the general formula (I), the compound in which R is —CO—CH$_2$—CH$_3$ is herein referred to as "Antibiotic C-15003 P-2" or more briefly as "P-2"; the compound in which R is

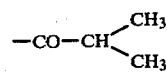

is herein referred to as "Antibiotic C-15003 P-3" or more briefly as "P-3"; the compound in which R is —CO—CH$_2$—CH$_2$—CH$_3$ is herein referred to as "Antibiotic C-15003 P-3'" or, more briefly, as "P-3'"; the compound in which R is

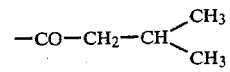

is herein referred to as "Antibiotic C-15003 P-4" or, more briefly, as "P-4".

As an example of the Antibiotic C-15003-producing strain of microorganism, there may be mentioned an actinomycete Strain No. C-15003 hereinafter sometimes abbreviated as "Strain No. C-15003" which was isolated from soil and other samples in screening for antibiotic-producing microorganisms.

The microbiological characters of Strain No. C-15003 were investigated by procedures analogous to those proposed by Schirling & Gottlieb [International Journal of Systematic Bacteriology 16, 313–340 (1966)]. The results of observations at 28° C. over 21 days are as follows.

(1) Morphological characters

The vegetative mycelium extends well and develops into branches, both on agar and in liquid medium. Many of the hyphae measure 0.8 to 1.2 μm in diameter and, in certain instances, may divide into fragments resembling rod bacteria or branched hyphae of short length. The strain gives good growth on various taxonomical media, with aerial mycelium being superimposed on the vegetative mycelium, although it frequently forms coremia like bodies (50–200×200–1000 μm) on which further aerial growth takes place. Many of the aerial mycelia are flexuous, straight or a loosely spiral like configuration being encountered on a few occasions. Microscopic examination of aged cultures reveals that only in few cases the conidia like cells occur in chains, while the cell suspensions obtained from the surfaces of such cultures, as microscopically examined, contained many elongated ellipsoidal (0.8–1.2 μm×4.8–6.8 μm) and ellipsoidal (0.8–1.2×1.0–2.0 μm) bodies resembling arthrospores.

Electron-microscopic examinations showed that these bodies had smooth surfaces.

(2) The constituents of cells

The strain was shake-cultured in modified ISP No.1 medium at 28° C. for 66 to 90 hours, at the end of which time the cells were collected and rinsed. By the method of B. Becker et al. [Applied Microbiology 12, 421 (1964)] and the method of M. P. Lechevalier [Journal of Laboratory and Clinical Medicine 71, 934 (1968)], the above whole cells were examined for diaminopimelic acid and sugar composition. The former was found to be the meso-form, while spots were detected which corresponded to galactose and arabinose.

(3) Characteristics on taxonomical media

The strain showed comparatively good growth on various media, with the vegetative mycelium being colorless to pale yellow in initial phases of culture and light yellowish tan to yellowish tan in later phases. The strain produces soluble pigments, yellow to yellowish tan, in various taxonomical media. The aerial mycelium is powdery and generally gives moderate growth, being white to yellow or light yellowish tan. The characteristics of the strain in various taxonomical media are set forth in Table 1.

TABLE 1

Cultural characteristics of Strain No. C-15003 on taxonomical media

(A) Sucrose nitrate agar:
   Growth (G): Moderate, Brite Melon Yellow (3 ia)* to Amber tan (3 1c)*, coremia like bodies formed
   Aerial mycelium (AM): Scant, white
   Soluble pigment (SP): None or pale yellowish tan (B) Glycerol nitrate agar:
   G: Moderate, Lt Ivory (2 ca)*, coremia like bodies formed
   AM: Moderate, white
   SP: None (C) Glucose asparagine agar:
   G: Moderate, Brite Marigold (3 pa)* to Brite Yellow (2 pa)*.
   AM: Scant, white
   SP: Brite Yellow (2 pa)*

(D) Glycerol asparagine agar:
   G: Moderate, Lt Ivory (2 ca)*, coremia like bodies formed
   AM: Scant, white
   SP: None (E) Starch agar:
   G: Moderate, Lt Ivory (2 ca)* to Lt Wheat (2 ea)*, coremia like bodies formed
   AM: Abundant, Lt Ivory (2 ca)*
   SP: None (F) Nutrient agar:
   G: Moderate, Lt Ivory (2 ca)* to Colonial Yellow (2 ga)*, coremia like bodies formed
   AM: Scant, white
   SP: None (G) Calcium malate agar:
   G: Moderate Lt Ivory (2 ca)* to Lt Wheat (2 ea)*, coremia like bodies formed.
   AM: Moderate, white to Lt Ivory (2 ca)*
   SP: None (H) Yeast extract-malt extract agar:
   G: Moderate, Amber (3 1c)* to Brite Yellow (3 1a)*, coremia like bodies formed
   AM: Moderate, white to Lt Ivory (2 ca)*
   SP: None (I) Oatmeal agar:
   G: Moderate, Lt Ivory (2 ca)* to Colonial Yellow (2 ga)*, coremia like bodies formed
   AM: Scant, white to light yellow
   SP: None (J) Peptone yeast extract iron agar:
   G: Moderate, Colonial Yellow (2 ga)*
   AM: None
   SP: Colonial Yellow (2 ga)*

(K) Tyrosine agar
   G: Moderate, Lt Ivory (2 ca)* to Lt Melon Yellow (3 ea)*, coremia like bodies formed.
   AM: Moderate, white to Lt Ivory (2 ca)*
   SP: Camel (3 ie)*

*The color codes according to Color Harmony Manual, 4th Ed. (Container Corporation of America, 1958).

(4) Physiological characters

The physiological characters of the strain are shown in Table 2. Temperature range for growth: 12° C. to 38° C. The temperature range in which good aerial growth occurs on agar (ISP No. 2) is 20° to 35° C.

TABLE 2

The physiological characters of Strain No. C-15003.

Temperature range for growth: 12 to 38° C.
Temperature range for aerial growth: 20 to 35° C.
Liquefaction of gelatin: Positive
Hydrolysis of starch: Positive
Reduction of nitrates: Positive
Peptonization of milk: Positive
Coagulation of milk: Negative
Decomposition of casein: Positive
Production of melanoid pigments:
   Negative (peptone yeast extract iron agar),

TABLE 2-continued

The physiological characters of Strain No. C-15003.

positive (tyrosine agar)
Decomposition of tyrosine: Positive
Decomposition of xanthine: Negative
Decomposition of hypoxanthine: Negative
Tolerance to lysozyme: Positive
Tolerance to sodium chloride: 2%

(5) Utilization of various carbon sources

The utilization of various carbon sources was investigated using a medium described in Pridham and Gottlieb [Journal of Bacteriology 56, 107 (1948)] and a basal medium of the same composition plus 0.1% of yeast extract. The resultant spectrum is shown in Table 3.

TABLE 3

The utilization of carbon sources by Strain No. C-15003

| Source of carbon | Growth | | Sources of carbon | Growth | |
|---|---|---|---|---|---|
| D-Xylose | + | ++* | Raffinose | ± | ±* |
| L-Arabinose | + | + | Melibiose | + | + |
| D-Glucose | ++ | ++ | i-Inositol | − | − |
| D-Galactose | + | + | D-Sorbitol | − | − |
| D-Fructose | +++ | ++ | D-Mannitol | ++ | ++ |
| L-Rhamnose | + | + | Glycerol | − | ± |
| D-Mannose | +++ | ++ | Soluble starch | + | + |
| Sucrose | ++ | ++ | Control | − | − |
| Lactose | − | − | | | |
| Maltose | ± | + | | | |
| Trehalose | + | ++ | | | |

*Basal medium with 0.1% yeast extract added
Note:
+++: Luxuriant growth
++: Good growth
+: Growth
±: Poor growth
−: No growth (6) Other characteristics The cells were harvested by the procedure previously described in (2) and DNA was prepared by a procedure analogous to that of J. Marmur et al. [Journal of Molecular Biology 3, 208, 1961]. The G-C (guanine-cytosine) content of the DNA was found to be about 71 mole %.

Gram-staining of the vegetative mycelium of this strain was positive.

The above characteristics of Strain No.C-15003 were compared with the descriptions in S. A. Waksman's "The Actinomycetes Vol.2" [The Williams and Wilkins Co., 1961]; R. E. Buchanan and N. E. Gibbons, "Bergey's Manual of Determinative Bacteriology, 8th Ed., 1974"; and other literatures.

Whilst this strain was thought to belong to Group III of genus Nocardia, the failure to find any species having the characters so far described among the known species led us to conclude that this strain represented a novel species of microorganism.

The present Strain No. C-15003 has been deposited at Fermentation Research Institute, Agency of Industrial Science and Technology (FERM), Japan under the accession number of FERM-P No. 3992; at The Institute for Fermentation, Osaka (IFO), Japan under the accession number of IFO 13726 and at The American Type Culture Collection (ATCC), Maryland, U.S.A. under the accession number of ATCC-31281.

While a microorganism of the genus Nocardia is liable, as are microorganisms generally, to undergo variations and mutations, either spontaneously or artificially.

For example, the many variants of the strain which are obtainable by irradiation with X-ray, gamma rays, ultra-violet light, etc., by single cell isolation, by culture on media containing various chemicals, or by any other mutagenic treatment, as well as the mutants spontaneously derived from the strain, should not be considered to represent any other distinct species but, rather, any of such variants and mutants capable of producing C-15003 P-2, P-3, P-3' and/or P-4 may be invariably utilized for the purposes of this invention. By way of example, subjecting Strain No. C-15003 to various mutagenic treatments yields mutants substantially lacking the ability to produce soluble pigments, mutants with substrate mycelia which are colorless, yellowish green, reddish tan or orange-red, mutants whose hyphae are ready to fragment into bacillary elements or branched short hyphal fragments, and mutants with abundant white aerial mycelia or substantially without aerial mycelia.

Leucine, as an additive substance in the present invention, may be used as a form of derivative. Examples of the derivatives are alkyl esters having one to 2 carbon atoms (e.g. methyl ester, ethyl ester) of leucine, amides such as amide, alkyl amides having one to 2 carbon atoms (e.g. N-methyl amide, N-ethyl amide) of leucine, its keto-acids (e.g. α-ketoisocaproic acid), or salts of the above compounds (e.g. hydrochloride). L-form of leucine is desirable. The mixtures of free form of leucine and its derivatives or a mixture of derivatives may also be employable.

In the practice of this invention, the aforesaid substances are generally added to the medium about 0.01 to 1.0% (W/V), preferably about 0.1 to 0.5% (W/V) at any time of the cultivation as long as the cultivation of Nocardia sp. No. C-15003 are carried out, preferably at the initial stage of the cultivation.

The medium employed for the cultivation of such an Antibiotic C-15003 P-4-producing strain may be whichever of a liquid and a solid medium only if it contains nutrients which the strain may utilize. For high-production runs a liquid medium is generally preferred.

The medium may comprise the additive substance used in the present invention, carbon and nitrogen sources which Antibiotic C-15003 P-4 producing strain may assimilate and digest, inorganic matter, trace nutrients, etc. As examples of said carbon sources may be mentioned glucose, lactose, sucrose, maltose, dextrin, starch, glycerol, mannitol, sorbitol, etc., fats and oils (e.g. soybean oil, lard oil, chicken oil, etc.) and so forth. The nitrogen sources may for example be meat extract, yeast extract, dried yeast, soybean meal, corn steep liquor, peptone, cottonseed flour, molasses, urea, ammonium salts (e.g. ammonium sulfate, ammonium chloride, amonium nitrate, etc.) and nitrate salts (e.g. sodium nitrate, potassium nitrate) so forth. The medium may further contain salts of sodium, potassium, calcium, magnesium, etc. salts of iron, manganese, zinc, cobalt, nickel, etc. and salts of phosphoric acid, boric acid, etc. Further, the medium may contain, as added, vitamins (e.g. $B_1$, $B_2$, nicotinic acid, $B_{12}$, C, E, etc.), nucleic acids, (e.g. purine, pyrimidine and derivatives thereof) and so forth. For the purpose of adjusting the pH of the medium, a mineral acid and/or an alkaline metal or ammonia as well as the corresponding bases as the pH-adjusting agents may be added. Furthermore oils and fats, surfactants, and antifoaming agents may also be added into the medium, if desired.

The cultivation may be conducted by any of the stationary, shaking, aerobic submerged and other cultural conditions. For high production runs, aerobic submerged culture is of course preferred. While the conditions of culture, of course, depends upon the condition of the fermentation and the composition of the medium, the strain, cultural method and other factors, it is normally preferred to carry out incubation at 20° to 35° C. with an initial pH of about 5.5-8.5 or thereabouts, particularly from 23° to 30° C. with an initial pH of 6.5 to 7.5. While the cultivation time is also variable according to the same factors as mentioned above, it is advisable to continue the cultivation until the potency of P-4 becomes maximal. In the case of shake culture or aerobic submerged culture in liquid medium, the time required normally ranges from about 48 to 240 hours.

The following is a concrete example of the method for the production of P-4.

Strain No. C-15003 was inoculated into a culture medium (I) composing 3% soluble starch, 0.2% ammonium chloride, 0.05% magnesium sulfate, 1.09% potassium dihydrogenphosphate, 2.09% dipotassium hydrogenphosphate, 0.001% ferrous sulfate and the additive substance, or a culture medium (II) comprising 5% dextrin, 3% corn steep liquor, 0.1% peptone, 0.5% calcium carbonate and the additive substance, and was cultivated at 28° C. for 144 hours on a rotary shaker (200 r.p.m.) or fermentor.

Table 4 and 5 show the results using the medium (I) and (II), respectively.

The potency of the total C-15003 was assayed with *Talaromyces avellaneus* IFO 7721 as an assay organism by paper disc method. The assay medium was consisting of 3.5 g of disodium hydrogen phosphate, 0.5% of potassium dihydrogen phosphate, 5 g of yeast extract (Difco, U.S.A.), 10 g of glucose, 15 g of agar and 1,000 ml of distilled water (pH 7.0).

The determination of P-2, P-3 and P-4 accumulated in the cultured broth was conducted as follows:

The cultured broth was extracted with the equal volume of ethyl acetate. The solvent layer was concentrated and dried. The dried matter was dissolved with ethyl acetate to give 1/100-volume of the starting broth. The products were developed on a silica-gel thin-layer chromatography (silica gel plate 60F$_{254}$, Merck, West Germany) with water-saturated ethyl acetate. The amount of the antibiotic and the ratio of the components were determined by Shimazu Dual-wave length TLC-scanner model CS-910 (Shimazu, Ltd., Japan) on the basis of the integral-densities of the each spot on the chromatogram at 254 nm. Ratio of the components was represented as weight-by-weight per cent in the total products, P-2, P-3 and P-4.

As shown in Table 4 and 5, Strain No. C-15003 produced the antibiotic P-4 in the ratio of 65% to 84% of the total in the presence of the specific additives, but 25% or less in the absence of such the components. Therefore, the recovery of P-4 from the cultured broth becomes more efficiently in the former case than that in the latter.

TABLE 4

| | | Ratio of the components (W/W %) | | | |
|---|---|---|---|---|---|
| Additive substance | Amount of addition (%) | Time of addition (hour)* | Ratio of the components (%) P-2 | P-3 | P-4 | Total potency (μg/ml) |
| Not added | — | — | 10 | 65 | 25 | 10 |

TABLE 4-continued

| | Ratio of the components (W/W %) | | | | |
|---|---|---|---|---|---|
| Additive substance | Amount of addition (%) | Time of addition (hour)* | Ratio of the components (%) P-2 | P-3 | P-4 | Total potency ($\mu$ g/ml) |
| L-leucine | 0.1 | 0 | 5 | 28 | 67 | 13.5 |
| L-leucine | 0.3 | 0 | 8 | 13 | 79 | 11.5 |
| L-leucine | 0.1 | 72 | 5 | 30 | 65 | 10 |

*Zero time means that the additive substance was added into the medium as the one of the ingredients.

TABLE 5

| | Ratio of the components (W/W %) | | | | |
|---|---|---|---|---|---|
| Additive substance | Amount of addition | Time of addition (hour)* | Ratio of the components (%) P-2 | P-3 | P-4 | Total potency ($\mu$ g/ml) |
| Not added | — | — | 15 | 60 | 25 | 18 |
| L-leucine | 0.3 | 0 | 7 | 21 | 72 | 20 |
| L-leucine | 0.5 | 0 | 5 | 11 | 84 | 15 |

*Zero time has the same meaning as the Note of Table 4.

Because P-4 which is thus produced in the fermentation broth, is lipophyl neutral substance, it can be conveniently recovered from the cultured broth by separation and purification procedures which are ordinarily employed for the recovery of such microbial metabolites. P-4 is easily extracted from the culture filtrate into water-immiscible organic solvents such as fatty acid esters, e.g. ethyl acetate and amyl acetate; alcohols, e.g. butanol; halogenated hydrocarbons, e.g. chloroform; and ketones, e.g. methyl isobutyl ketone. The extraction of P-4 from the filtrate is carried out at a pH near neutral, preferably, with ethyl acetate at pH 7. The extract is washed with water and concentrated under reduced pressure. Then, a nonpolar solvent such as petroleum ether or hexane is added to the concentrate and the crude product containing the active compound is recovered as precipitates. The crude product is sequentially subjected to convenient purification procedures, if desired. Thus, as a routine purification procedure, adsorption chromatography is useful and, for this purpose, one of those common adsorbents such as silica gel, active alumina, macroporous nonionic adsorbent resin, etc. may be employed. P-4 in the crude product is developed on such the silica-gel chromatography with, for example, with petroleum ether and hexane and eluted by the addition of a polar solvent such as ethyl acetate, acetone, ethanol or methanol or a halogenated hydrocarbon such as dichloromethane or chloroform, containing a polar solvent such as an alcohol, e.g. methanol or ethanol, a ketone, e.g. acetone or methyl ethyl ketone, or the like. In this way, P-4 is eluted, separated and recovered.

In the case that a macroporous adsorbent resin is used for the purification of P-4, elution of P-4 from the column is accomplished with a mixture of water with a lower alcohol, a lower ketone or an ester. The lower alcohol may for example be methanol, ethanol, propanol or butanol, etc., and the lower ketone may for example be acetone or methyl ethyl ketone, etc. The ester may for example be ethyl acetate butylacetate, etc. In a typical procedure, the crude product II is dissolved in 60% methanol-water and adsorbed on a column of Diaion HP-10 (Mitsubishi Chemical Industries Ltd., Japan). The column is washed with 70% methanol-water and, P-4 is eluted with 90% methanol-water.

In the process described above, the fractions containing P-4 are pooled and concentrated under reduced pressure. To the dry product is added 5 to 8 volumes of ethyl acetate and the mixture is allowed to stand, whereupon crystals of P-4 separates.

In the method of the present invention, the production ratio of P-4 in the C-15003 products reaches about 65% or more and P-4 is easily recovered from the cultured broth. Therefore, the method of the present invention is very advantageous for an industrial production of P-4.

The physico-chemical properties of P-4 obtained in Example 4 are shown in Table 6.

TABLE 6

| Antibiotic C-15003 P - 4 $C_{33}H_{45}ClN_2O_9 = 649.196$ | |
|---|---|
| Melting point (°C.) | 177–180° |
| Specific rotation $[\alpha]_D^{22°}$ | $-142° \pm 10°$ (C = 0.522 CHCl$_3$) |
| Elemental analysis Found (%) | C 60.65 |
| | H 7.05 |
| | N 4.25 |
| | Cl 5.23 |
| Elemental analysis Calc. (%) | C 61.05 |
| | H 6.99 |
| | N 4.32 |
| | Cl 5.46 |
| Ultraviolet absorption spectra nm($\epsilon$) (in methanol) | 233(29900) 240(sh 28240) 252(27590) 280(5712) 288(5680) |
| Infrared absorption spectra (cm$^{-1}$) KBr | 1740, 1730, 1670, 1580 1445, 1385, 1340, 1255, 1180, 1150, 1100, 1080, 1038 |
| Nuclear Magnetic resonance spectra (ppm) 100 MHz in CDCl$_3$ | 1.03(d) (6H) |
| Mass spectra (m/e) | 587, 485, 470, 450 |
| Solubility | Insoluble in petr. ether, hexane, water. Sparingly soluble in benzene, ether. Soluble in chloroform, ethyl acetate, acetone, ethanol, methanol, pyridine, tetrahydrofuran, dimethylsulfoxide. |
| Color reactions | Dragendorff: Positive Beilstein: Positive |

It is assumed that P-3, P-3' and P-4 are novel compounds, but P-2 is the same compound as maytansinol propionate which is shown in Kupchan et al's report [The Journal of American Chemical Society 97, 5294(1975)] in terms of elemental analysis, specific rotation, ultraviolet ray absorption, infra red ray absorption, mass spectrum and so forth.

Biological activity of P-4 is as follows:

(A) Antimicrobial activity:

With trypticase-soy agar (BBL) as an assay medium, the inhibitory concentrations against the microorganisms described below were investigated by the paper disc method. Thus, filter-paper discs (Toyo Seisakusho, thin-type, 8 mm in dia.) each impregnated with 0.02 ml of a 300 $\mu$g/ml solution of P-4 were placed on agar plates respectively inoculated with the microorganisms described below. P-4 had no activity against the following bacteria. *Escherichia coli, Proteus vulgaris, Proteus mirabilis, Pseudomonas aeruginosa, Staphylococcus aureus, Bacillus subtilis, Bacillus cereus, Klebsiella*

*pneumoniae, Serratia marcescens* and *Mycobacterium avium*

On the other hand, the growth of a fungus, Talaromyces avellaneus is inhibited by P-4 on an agar plate consisting of 3.5 g disodium hydrogen phosphate, 0.5 g monopotassium dihydrogen phosphate, 5 g yeast extract (Difco), 10 g glucose, 15 g agar, 1,000 ml distilled water, pH 7.0. The minimal inhibitory concentration was 1.0 to 1.5 μg/ml for P-4. Furthermore, *Tetrahymena pyriformis* W was cultivated on an assay medium [composed of 20 g Proteosepeptone (Difco), 1 g yeast extract, 2 g glucose, 1,000 m distilled water and 10 ml 1 M-phosphate buffer pH 7.0] at 28° C. for 44 to 48 hours and the growth inhibitory activity of P-4 against the protozoa was determined by the serial dilution method. Growth inhibition occured at 0.5 μg/m for C-15003 P-4.

P-4 had the activity against the following microorganisms:

*Fusicladium levieri, Helminthosporium sigmoidium var. irregulare, Pyricularia oryzae, Cochlioborus miyabeanus, Sclerotinia screrotiorum, Pellicularia sasakii, Trichophyton rubrum, Rhodotorula ruba* and *Cryptococcus neoformans.*

(B) Antitumour activity

The therapeutic effects of P-4 (dosed intraperitoneally for 9 consecutive days) upon P388 leukemia in mice ($1 \times 10^6$ cells/animal, mouse, intraperitoneally transplanted) was investigated. P-4 had an antitumour activity as high as 180% life-span-extending ratio at the dose level of 0.00625 mg/kg/day.

(C) Toxicity

In a preliminary acute toxicity test with mice as test animals, which involved intraperitoneal injections of P-4. This antibiotic showed a $LD_{50}$ value more than 0.313 mg/kg.

As mentioned hereinbefore, P-4 has strong inhibitory activity against fungi and protozoa and, therefore, is of value as an antifungal or antiprotozoan agent. Furthermore, because P-4 displays a life span-extending action upon tumour-bearing mammalian animals (e.g. mouse), it is also expected that the compound will be of use as an antitumour drug.

P-4, as an antifungal and antiprotozoan agent, can be used with advantage for an assessment of the bacterial ecology in soil, active sludge, animal body fluid or the like. Thus, when valuable bacteria are to be isolated from soil samples or when the actions of bacteria are to be evaluated independently of those of fungi and protozoa in connection with the operation and analysis of an active sludge system used in the treatment of waste water, as the present antibiotic may be utilized to obtain a selective growth of the bacterial flora without permitting growth of the concomitant fungi and protozoa in the specimen. In a typical instance, the sample is added to a liquid or solid medium and 0.1 ml of a 10 to 100 μg/ml solution of P-4 in 1% methanol-water is added per ml of the medium, which is then incubated.

P-4 can also be used as an anti-microbial agent for the treatment of plant diseases caused by the microorganisms mentioned in the above. In the typical application, P-4 is used in a form of 1% methanolic aqueous solution containing 0.5 μg/ml–5 μg/ml of the antibiotic. For instance P-4 may be used for the control of the blast, the Helminthosporium leaf spot and the sheath blight of rice plants.

The following examples are further illustrative to explain the present invention in detail, wherein "part(s)" is based on weight unless otherwise noted and the relationship between "part(s)" and "part(s) by volume" corresponds to that between "gram(s)" and "milliliter(s)", and "%" is based on "weight/volume" unless otherwise noted.

EXAMPLE 1

Forty parts by volume of seed culture medium (1.0% glucose, 2.0% Bacto-trypton and 1.2% Bacto-yeast extract, pH 7.0) is poured into 200 parts by volume of Erlenmeyer flask.

After sterilization, Nocardia sp. No. C-15003 (IFO 13726; ATCC 31281: FERM-P No.3992) was inoculated to the medium. The inoculant was incubated at 28° C. on a rotary shaker (200 r.p.m.) to give a seed culture. The cells in culture was washed three times with sterilized distilled water, and the washed cells were re-slurried in the original broth volume of sterilized distilled water.

One part by volume of the above was inoculated into 40 parts by volume of a main culture medium consisting of 3% soluble starch, 0.2% ammonium chloride, 0.05% magnesium sulfate, 1.09% potassium dihydrogenphosphate, 2.09% dipotassium hydrogenphosphate, 0.001% ferrous sulfate and 0.3% L-leucine, and the main culture was conducted at 28° C. for 8 days on the rotary shaker (200 r.p.m.)

The total production amount of C-15003 was 12 μg/ml, and the ratio of P-4 in the total was 80% (W/W).

EXAMPLE 2

500 parts by volume of the seed culture, as shown in Example 1 was inoculated into 2,000 parts by volume of Sakaguchi flask and cultivated at 28° C. for 48 hours on a reciprocal shaker (110 strokes/min.) to give an inoculum. The inoculum was transferred to $100 \times 10^3$ parts by volume of a medium consisting of 2.0% glucose, 3.0% soluble starch, 1.0% corn steep liquor, 1.0% soybean flour, 0.5% Polypepton (Daigo Nutritive Chemicals, Ltd., Japan), 0.3% sodium chloride, 0.5% calcium carbonate W/V, pH 7.0) in $200 \times 10^3$ parts by volume of a stainless steel fermentor.

The culture was conducted at 28° C., for 48 hours under 100 l/minute aeration and 200 r.p.m. agitation. The culture broth ($10 \times 10^3$ parts by volume) was transferred to $100 \times 10^3$ parts by volume of a fermentation medium (5% dextrin, 3% corn steep liquor, 0.1% peptone, 0.5% L-leucine and 0.5% calcium carbonate (W/V), pH 7.0) in $200 \times 10^3$ parts by volume of the stainless steel fermentor.

The fermentation was carried out at 28° C. for 4 days under $100 \times 10^3$ parts by volume/minute aeration, 150 r.p.m. agitation.

The total production amount of C-15003 was 12 μg/ml, and P-4 in C-15003 was about 85% (W/W).

EXAMPLE 3

To $95 \times 10^3$ parts by volume of the cultured broth obtained in Example 2 is added $50 \times 10^3$ parts by volume of acetone. The mixture is stirred for 30 minutes. To the resultant is added $2 \times 10^3$ parts of Hyflo Super-Cel (Johnes and Manville Products, Ltd.) and the mixture is stirred well.

The mixture was filtered with on a pressure filter to give $135 \times 10^3$ parts by volume of filtrate. To the filtrate was added $50 \times 10^3$ parts by volume of water and $90 \times 10^3$ parts by volume of ethyl acetate, and the mixture was stirred and extracted twice.

The obtained ethyl acetate layer were combined and washed twice with water of $80 \times 10^3$ parts by volume each. To the ethyl acetate layer obtained was added $1 \times 10^3$ parts of anhydrous sodium sulfate, dried and concentrated to 200 parts by volume. To the concentrate was added petroleum ether, and emerged precipitate was recovered by filtration to give 35 parts of the crude product.

To thus obtained crude product was added 50 parts by volume of ethyl acetate and the mixture was stirred.

The insolubles were removed by filtration and to the filtrate is added 10 parts of silica gel (Merck, West Germany, 0.05 to 0.2 mm). After stirring the mixture, ethyl acetate was removed by distillation under reduced pressure. The residue was applied to the top of a silica gel column (500 parts by volume). The antibiotics was eluted stepwise with 500 parts by volume of n-hexane, 500 parts by volume of a mixture of n-hexane-ethyl acetate (3:1), 2,000 parts by volume of a mixture of n-hexane-ethyl acetate (1:1), and 2,000 parts by volume of water saturated ethyl acetate, and the eluate were collected in 50 parts by volume fractions, each.

One part by volume portion of each fraction was concentrated to dryness, and 0.1 part by volume of ethyl acetate was added to the concentrate to give a mixture. The mixture was spotted at 2.5 cm from the bottom edge of a silica gel-glass plate (Merck, West Germany, 60 $F_{254}$, 0.25 mm, 20×20) and developed for about 17 cm with water saturated ethyl acetate. After development, detection was carried out with ultraviolet light (2357Å). The active fractions of Rf 0.49 were collected and concentrated under reduced pressure to above 2 parts by volume. To this concentrate was added 20 parts by volume of petroleum ether to obtain 1.08 parts of a crude crystals. The crude crystals was dissolved in 20 parts by volume of warm ethyl acetate. After cooling, 0.92 part of P-4 were recovered. The purity of P-4 crystals obtained was 94% (W/W) and its melting point was 178°–180° C.

EXAMPLE 4

In 400 parts by volume of 50% methanol was dissolved 20 parts of the crude product obtained in Example 3. 1,000 parts by volume of Diaion HP-10 (Mitsubishi Chemical Industries Ltd., Japan) was packed into a column (2.5 cm in dia.) with 3,000 parts by volume of 50% methanol-water. The sample solution prepared above was passed through the column and washed with 1000 parts by volume of 60% methanol, and gradient eluthion was carried out continuously using 7,500 parts by volume of 60% methanol-water and 7,500 parts by volume of 95% methanol-water.

The eluate was collected in 75 parts by volume fractions and each fraction was applied in the silica gel thin layer chromatography described in Example 3.

The active fractions Nos. 182 to 190 were collected and concentrated. To the concentrate were added 500 parts by volume of water and 1,000 parts by volume of ethyl acetate.

The mixture was shaken in a separatory funnel and the water layer was separated, and after washing twice with 300 parts by volume of water, the ethyl acetate layer was dried over anhydrous sodium sulfate, concentrated and allowed to stand.

The resulting crystal of P-4 were collected by filtration and dried (0.950 part of P-4).

The purity of P-4 crystals obtained was 92% W/W and its melting point was 177° to 179° C.

EXAMPLE 5

Methyl ester of leucine, N-methyl amide of leucine, α-ketoisocaproic acid or hydrochloride of leucine is used in place of L-leucine in Example 1, whereby similar results, i.e. specific production of the objective P-4, are obtained respectively.

What we claim is:

1. In a method for producing Antibiotic C-15003 P-4 by cultivating a microorganism belonging to the genus Nocardia and being capable of producing Antibiotic C-15003 P-4 in a culture medium containing assimiable carbon sources and digestible nitrogen sources, wherein the improvement comprises incorporating about 0.01 to 1% by weight based on the volume of the culture medium of leucine, α-ketoisocaproic acid or its salt, or an ester, amide or salt of leucine as additive substances into the culture medium.

2. A method as claimed in claim 1, wherein the microorganism is Nocardia sp. No. C-15003 (ATCC-31281; IFO 13726; FERM-P No. 3992).

3. A method as claimed in claim 1, wherein the additive substance is leucine.

* * * * *